United States Patent
Park et al.

(10) Patent No.: US 10,486,909 B2
(45) Date of Patent: Nov. 26, 2019

(54) ITEM TRANSFER APPARATUS, ITEM INSPECTION APPARATUS, ITEM TRANSFER METHOD, AND ITEM INSPECTION METHOD

(71) Applicant: KOH YOUNG TECHNOLOGY INC., Seoul (KR)

(72) Inventors: Nam Kyu Park, Namyangju-si (KR); Joo Hyuk Kim, Uijeongbu-si (KR); Ho Jun Lee, Bucheon-si (KR)

(73) Assignee: KOH YOUNG TECHNOLOGY INC., Seoul (KR)

( * ) Notice: Subject to any disclaimer, the term of this patent is extended or adjusted under 35 U.S.C. 154(b) by 0 days.

(21) Appl. No.: 15/770,308

(22) PCT Filed: Oct. 27, 2016

(86) PCT No.: PCT/KR2016/012194
§ 371 (c)(1),
(2) Date: Apr. 23, 2018

(87) PCT Pub. No.: WO2017/074075
PCT Pub. Date: May 4, 2017

(65) Prior Publication Data
US 2018/0297784 A1    Oct. 18, 2018

(30) Foreign Application Priority Data
Oct. 30, 2015  (KR) ........................ 10-2015-0152321

(51) Int. Cl.
*B65G 21/10*    (2006.01)
*B65G 37/00*    (2006.01)
(Continued)

(52) U.S. Cl.
CPC ............. *B65G 21/10* (2013.01); *B65G 37/00* (2013.01); *B65G 43/00* (2013.01); *B65G 47/22* (2013.01);
(Continued)

(58) Field of Classification Search
CPC .... B65G 47/24; B65G 47/244; B65G 47/252; B65G 21/10; B65G 37/00; B65G 47/22;
(Continued)

(56) References Cited

U.S. PATENT DOCUMENTS 4,457,419 A    7/1984  Ogami et al.
4,573,863 A *  3/1986  Picotte ................. B65G 47/252
                                                        198/403
(Continued)

FOREIGN PATENT DOCUMENTS

EP    0 296 096    12/1988
EP    2 246 276    11/2010
(Continued)

OTHER PUBLICATIONS

International Search Report for International Application No. PCT/KR2016/012194, dated Jan. 26, 2017.
(Continued)

*Primary Examiner* — James R Bidwell
(74) *Attorney, Agent, or Firm* — Kile Park Reed & Houtteman PLLC

(57) ABSTRACT

An item transfer apparatus according to the present invention is for transferring items and comprises: a switching part for switching the front and rear surfaces or top and bottom surfaces of the items with respect to the transfer direction of the item; a transferring part for transferring the items to the switching part; and a rotating part for rotating the items while maintaining the top and bottom surfaces of the items.

20 Claims, 17 Drawing Sheets

(51) Int. Cl.

| | | |
|---|---|---|
| *B65G 47/22* | (2006.01) | |
| *B65G 47/244* | (2006.01) | |
| *G01N 21/89* | (2006.01) | |
| *B65G 43/00* | (2006.01) | |
| *G01B 11/00* | (2006.01) | |
| *G01N 21/88* | (2006.01) | |
| *B65G 47/252* | (2006.01) | |
| *G01N 21/95* | (2006.01) | |
| *G01N 21/84* | (2006.01) | |

(52) U.S. Cl.
CPC ......... *B65G 47/244* (2013.01); *B65G 47/252* (2013.01); *G01B 11/00* (2013.01); *G01N 21/88* (2013.01); *G01N 21/8901* (2013.01); *G01N 21/95* (2013.01); *G01N 2021/845* (2013.01)

(58) Field of Classification Search
CPC ........ B65G 43/00; B65H 15/00; B65H 15/02; G01N 21/8901; G01N 21/89
USPC ................................. 198/403, 406, 407, 414
See application file for complete search history.

(56) References Cited

U.S. PATENT DOCUMENTS

| | | | | |
|---|---|---|---|---|
| 4,798,278 A | | 1/1989 | Cornacchia | |
| 5,141,095 A | * | 8/1992 | Kamp | ................... B65H 67/064 198/409 |
| 5,317,859 A | * | 6/1994 | Schneider | ............... B65B 5/106 53/251 |
| 6,142,287 A | * | 11/2000 | Biffert | ................... B65G 47/252 198/402 |
| 7,909,156 B2 | * | 3/2011 | Wen | ..................... B65G 49/067 198/346.1 |
| 8,172,071 B2 | * | 5/2012 | Schafer | ................ B65G 47/244 198/412 |
| 8,550,228 B1 | * | 10/2013 | Wei | ........................ A21C 9/085 198/411 |
| 2014/0267691 A1 | | 9/2014 | Humphrey et al. | |

FOREIGN PATENT DOCUMENTS

| | | |
|---|---|---|
| JP | 56-003126 | 1/1981 |
| JP | 3-61400 | 6/1991 |
| JP | 4-77300 | 7/1992 |
| JP | 05-049730 | 6/1993 |
| JP | 06-082040 | 11/1994 |
| JP | 09-012133 | 1/1997 |
| JP | 09-052202 | 2/1997 |
| JP | 2753445 | 5/1998 |
| JP | 2000-97671 | 4/2000 |
| JP | 2000-233824 | 8/2000 |
| JP | 2006-7293 | 1/2006 |
| JP | 2010-194563 | 9/2010 |
| JP | 2011-006186 | 1/2011 |
| KR | 10-2009-0070926 | 7/2009 |
| KR | 10-1111272 | 2/2012 |

OTHER PUBLICATIONS

English translation of the Written Opinion of International Application No. PCT/KR2016/012194; dated May 1, 2018.
Extended European Search Report for European Application No. 16 86 0258, dated Oct. 19, 2018.
Japanese Office Action with English translation for Japanese Patent Application No. 2018-521106, dated Mar. 11, 2019.
Chinese Office Action with English translation for Chinese Application or Publication No. 201680062254.3, dated Jun. 5, 2019.

* cited by examiner

ITEM TRANSFER APPARATUS, ITEM INSPECTION APPARATUS, ITEM TRANSFER METHOD, AND ITEM INSPECTION METHOD

TECHNICAL FIELD

The present disclosure relates to an item transfer apparatus, an item inspection apparatus, an item transfer method, and an item inspection method.

BACKGROUND

In case of manufacturing items or assembling them with other items, it is essential to perform an inspection of the manufacturing or assembly condition of items in order to increase the reliability of products. An inspection method is known in which an item is visually inspected to determine whether the item is defective. As a method of inspecting items, a method of transferring items using a conveyor transfer belt to automatically transfer an object to be inspected, or a method of inspecting transferred items using an inspection apparatus may be adopted.

If the automatically transferred item is inspected using the inspection apparatus, only an upper surface of the item or upper and side surfaces of the item can be inspected, and there is the problem that it is impossible to inspect all surfaces of the item at one go. In this case, an operation to transition the top and bottom surfaces of the item is necessary, and this operation may transition manually or require an additional apparatus.

Conventionally, Korean Patent Registration No. 10-1111272 discloses an apparatus that inspects an upper surface and a side surface of an object to be inspected while transferring the object to be inspected by a transfer rail. This document relates to an apparatus for inspecting an exterior of a case of an electronic device, wherein upper and side surfaces are inspected using a plurality of cameras.

Since the inspection apparatus according to the related art inspects only the upper surface and the side surface of the object to be inspected (the case of the electronic device), it is necessary to transition the top and bottom surfaces of the object to be inspected when the bottom surface of the object to be inspected also needs to be inspected. The transitioning of item surfaces to be inspected needs to be performed manually or using an additional transitioning device. In such a case, since a corresponding operation needs to be performed at a front end or a rear end of the transfer rail, there is the problem that the length of the entire line becomes longer, the space efficiency is decreased, and a tact time becomes longer. In addition, since a measurement is performed using a plurality of cameras, the entire inspection apparatus becomes large and costs increase.

The present disclosure provides an item transfer apparatus that transfers items so that items can be inspected at a single line and an item inspection apparatus that can inspect items at a single line, and a compact item transfer apparatus and item inspection apparatus that have a high spacial efficiency and that can reduce the tact time.

SUMMARY

An item transfer apparatus according to one embodiment of the present disclosure is an apparatus that transfers an item and may include: a transitioning part configured to transition to front and rear surfaces or top and bottom surfaces of the item with respect to a transfer direction of the item; a transferring part configured to transfer the item to the transitioning part; and a rotating part configured to rotate the item while maintaining the top and bottom surfaces of the item.

According to one embodiment, the transitioning part may include a take-in and take-out part configured to take-in or take-out the item, an item transitioning part configured to transition the item while maintaining the item in the take-in and take-out part, and a fixing part on which the item transitioning part is fixed.

According to one embodiment, the fixing part includes first and second fixing frames, the item transitioning part includes first and second item transitioning frames that are respectively disposed on inner surfaces of the first and second fixing frames, the inner surfaces facing each other, an item transitioning actuator that is disposed on a first fixing frame and configured to transition the first and second item transitioning frames, and an item transitioning shaft that is linked with the item transitioning actuator, extended to pass through the first and second fixing frames, and linked with the first and second item transitioning frames, and the take-in and take-out part may include take-in and take-out pulleys that are disposed on inner surfaces of the first and second item transitioning frames, the inner surfaces facing each other, take-in and take-out belts that are linked with the take-in and take-out pulleys, and take-in and take-out actuators that are disposed on the first and second fixing frames and configured to drive the take-in and take-out pulleys.

According to one embodiment, the fixing part further includes an auxiliary transfer part that is located between the transferring part and the take-in and take-out part, and the auxiliary transfer part includes auxiliary transfer pulleys that are disposed on the first and second fixing frames and auxiliary transfer belts that are linked with the auxiliary transfer pulleys, and the auxiliary transfer pulleys are driven by the take-in and take-out actuators.

According to one embodiment, the transitioning part further includes an item fixing part that is disposed on at least one of the first and second item transitioning frames, and the item fixing part may include an item fixing shaft, an item fixing actuator that is connected to one end of the item fixing shaft and a fixed end that is connected to the item fixing shaft.

According to one embodiment, the item fixing part may further include a sensing part configured to detect whether the item is present or absent.

According to one embodiment, the rotating part may include a supporting part configured to support a bottom surface of the item located at the transferring part, a rotation actuation part configured to rotate the supporting part, and a raising-and-lowering part configured to raise and lower the item.

According to one embodiment, the supporting part includes a first rotation frame and a support that protrudes upwards from the first rotation frame, the rotation driving part includes a second rotation frame and a rotation actuator that is fixed to the second rotation frame and configured to rotate the first rotation frame, and the raising-and-lowering part may include a third rotation frame and a raising-and-lowering actuator that is fixed to the third rotation frame and configured to raise and lower the second rotation frame.

According to one embodiment, the transferring part may include a transfer frame, a transfer pulley that is disposed on the transfer frame, a transfer belt that is linked with the transfer pulley, and a transfer actuator configured to provide a driving force to the transfer pulley.

According to one embodiment, the transfer frame includes first and second transfer frames arranged in parallel, and the first transfer frame may include a position adjustment part configured to place the item at the first position.

According to one embodiment, the position adjustment part may include a position adjustment shaft, a position adjustment actuator that is fixed to the first transfer frame and configured to advance and retreat the position adjustment shaft, and a position adjustment end that is connected to the position adjustment shaft.

According to one embodiment, the item transfer apparatus may further include a width adjusting part.

According to one embodiment, the first transfer frame is connected to the first fixing frame, and the second transfer frame may be connected to the second fixing frame.

An item inspection apparatus according to one embodiment of the present disclosure includes the item transfer apparatus and may further include an inspecting part configured to inspect a shape of the item.

According to one embodiment, in the item inspection apparatus, the inspecting part may be located above the item transfer apparatus.

According to one embodiment, the item inspection apparatus may further include a height adjustment part configured to adjust a height of the transitioning part or the inspecting part.

According to one embodiment, the height adjustment part may include a support frame, and a height adjustment actuator that is fixed to the support frame and configured to adjust the height of the fixing part.

An item transfer method according to one embodiment of the present disclosure is a method for transferring an item and may include: transferring an item from an initial position; transitioning to front and rear surfaces and top and bottom surfaces of the item with respect to a transfer direction; returning the item in an opposite direction to the transfer direction in the state where the top and bottom surfaces of the item are transitioned; rotating the item while maintaining the top and bottom surfaces of the item; and repeating the act of transferring the item from the initial position and the act of transitioning to the front and rear surfaces and top and bottom surfaces of the item with respect to the transfer direction of the item.

According to one embodiment, the item transfer method may further include discharging the item in the transfer direction of the item, after the act of repeating the act of transferring the item from the initial position and the act of transitioning to the front and rear surfaces and top and bottom surfaces of the item with respect to the transfer direction of the item.

According to one embodiment, the act of rotating the item while maintaining the top and bottom surfaces of the item may include raising and lowering the item.

According to one embodiment, the act of rotating the item while maintaining the top and bottom surfaces of the item may rotate the item by 90 degrees.

An item inspection method according to one embodiment of the present disclosure is a method that inspects an item and may include: transferring an item from an initial position to a first position; inspecting a top surface of the item at the first position; inspecting the item by transitioning front and rear surfaces of the item to face upwards; transitioning a bottom surface of the item to face upwards; returning the item to the initial position; rotating the item by 90 degrees at the initial position while maintaining the top and bottom surfaces of the item; transferring the item again to the first position; inspecting the bottom surface of the item at the first position; and inspecting the item by transitioning left and right surfaces of the item to face upwards.

According to one embodiment, the item inspection method may further include discharging the item, after the act of inspecting the item by transitioning the left and right surfaces of the item to face upwards.

The item transfer apparatus and item inspection apparatus according to the present disclosure is configured to be compact, can transition the item within one transfer apparatus, and has the effect that an efficient space utilization is possible. In addition, it is possible to provide six surfaces of an item through one item transfer apparatus, and to inspect all surfaces of the item using only a small number of cameras.

DETAILED DESCRIPTION

Figure 1:
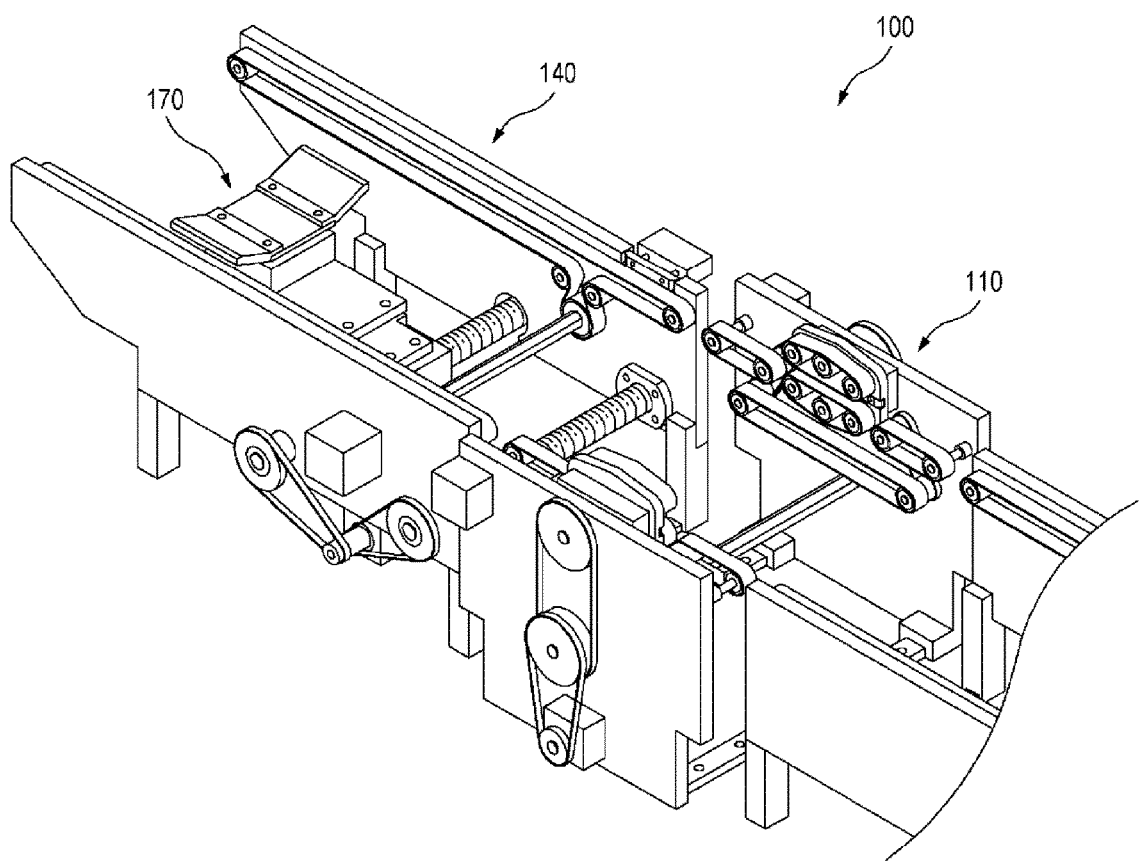
FIG. 1 is a perspective view of an item transfer apparatus according to the present disclosure.

Embodiments of the present disclosure described below are illustrated for the purpose of describing the present disclosure. The embodiments of the present disclosure can be implemented in various forms, and the scope of the present disclosure is not limited to the embodiments described below or to detailed description of the embodiments.

Unless otherwise defined, all technical and scientific terms used in the present disclosure have the meaning as generally understood by a person having ordinary skill in the art to which the present disclosure pertains. All terms used in the present disclosure are chosen for the purpose of describing the disclosure more clearly and are not chosen for limiting the scope of the present disclosure.

Unless otherwise stated, expressions in the singular form used in the present disclosure may include expressions in the plural form, and the same applies to expressions in the singular form used in the claims.

Expressions such as "first," "second" or the like used in various embodiments of the present disclosure, are used to distinguish a plurality of elements from one another, but not to restrict the order or importance of the corresponding elements.

Expressions such as "including" or "having" or the like used in the present disclosure, should be understood as open-ended terms that include the possibility of including other embodiments unless particularly otherwise stated in the phrase or sentence that includes the corresponding expressions.

In the present disclosure, the expression "based on" is used to describe one or more factors that affect a decision, or determination, or action that is described in the phrase which includes the corresponding expression, and does not exclude additional factors that affect the decision, or determination, or action.

In the present description, mentioning that one element is "connected" or "coupled" to another element should be understood that the one element may be directly connected or coupled to the other element, but a new further element may exist between the one element and the other element.

Hereinafter, embodiments of the present disclosure will be described in detail with reference to the accompanying drawings. The same reference numeral will be used for the same element throughout the drawings, and duplicate descriptions of the same element will be omitted.

FIG. 1 illustrates an item transfer apparatus 100 according to the present disclosure. The item transfer apparatus 100 includes a transitioning part 110 that transitions the item to front and rear surfaces or top and bottom surfaces with respect to the transfer direction, a transferring part 140 that transfers the item to the transitioning part 110, and a rotating part 170 that rotates the item while maintaining the top and bottom surfaces of the item. Hereinafter, as one embodiment, the item transfer apparatus 100 according to the present disclosure will be described in more detail.

Figure 2:
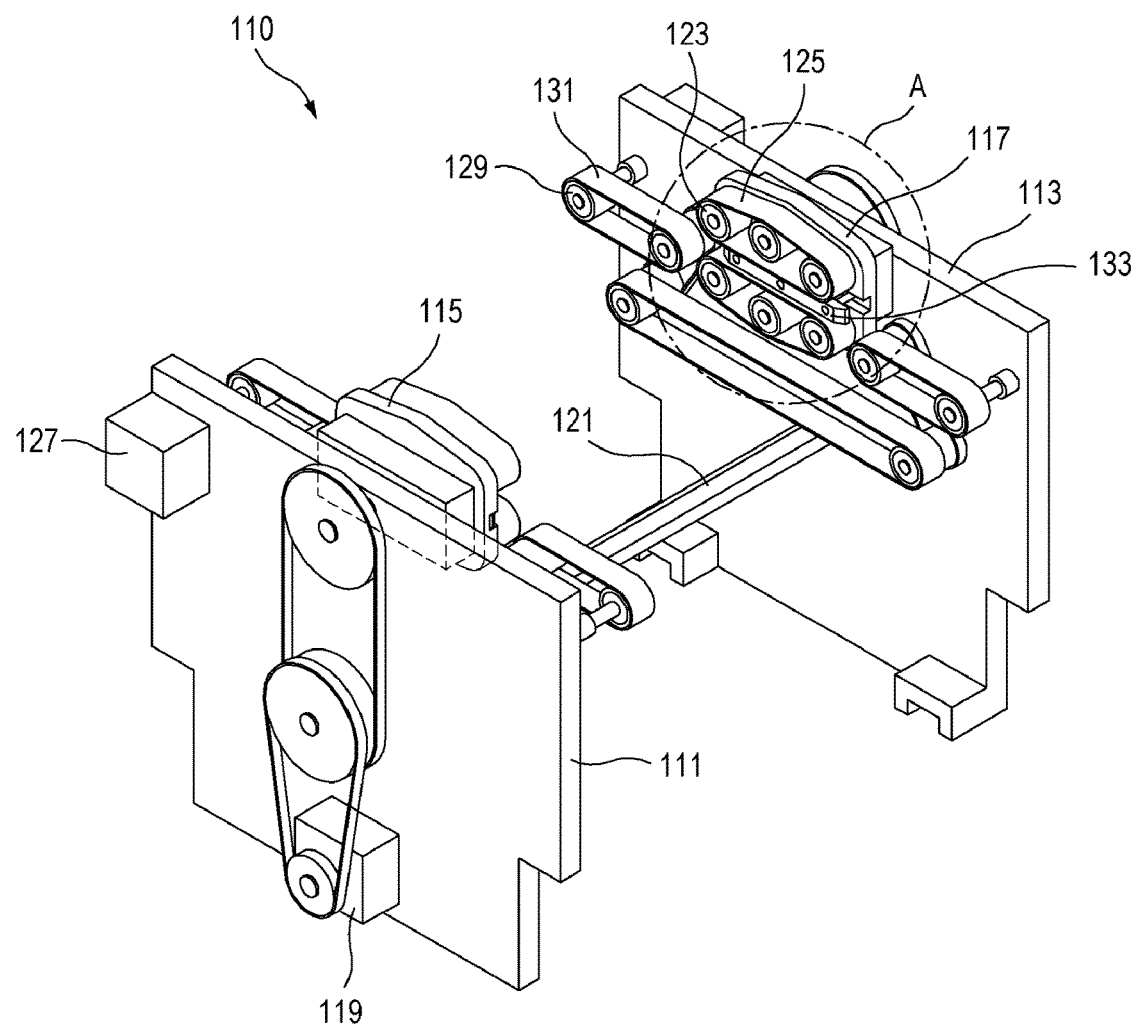
FIG. 2 is a perspective view of a transitioning part according to the present disclosure.
Figure 3:
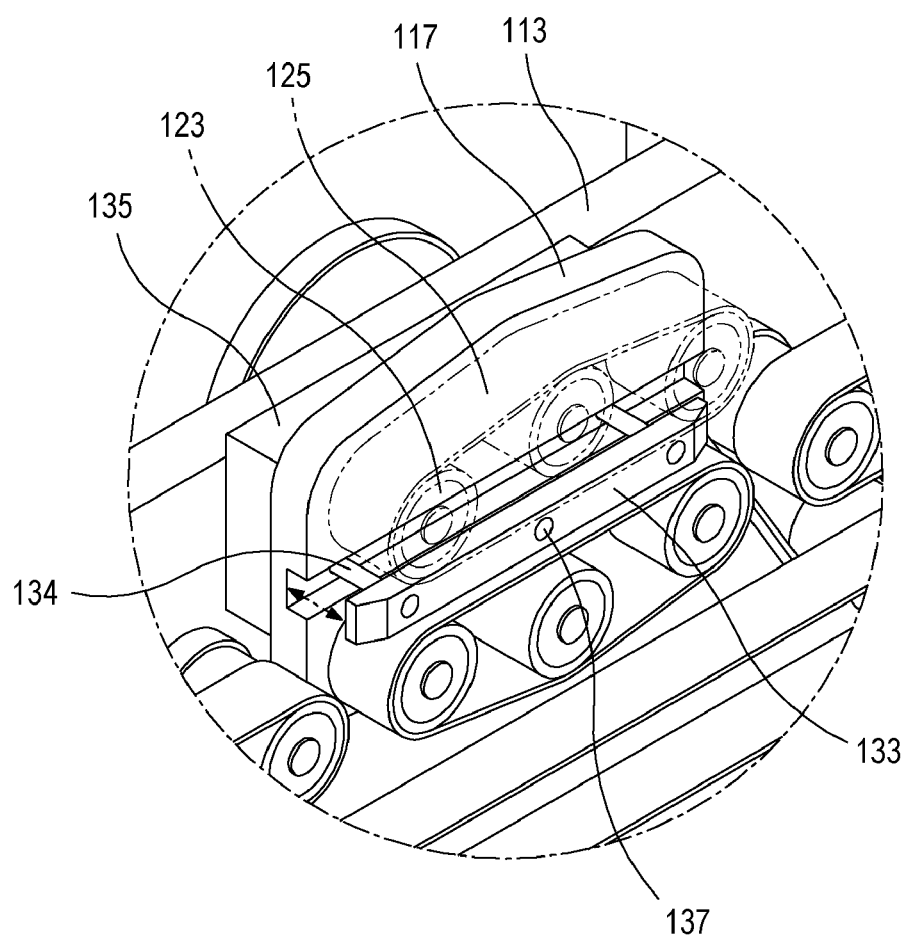
FIGS. 3 and 4 are a front perspective view and a front view of one side of an item transitioning part according to the present disclosure.
Figure 4:
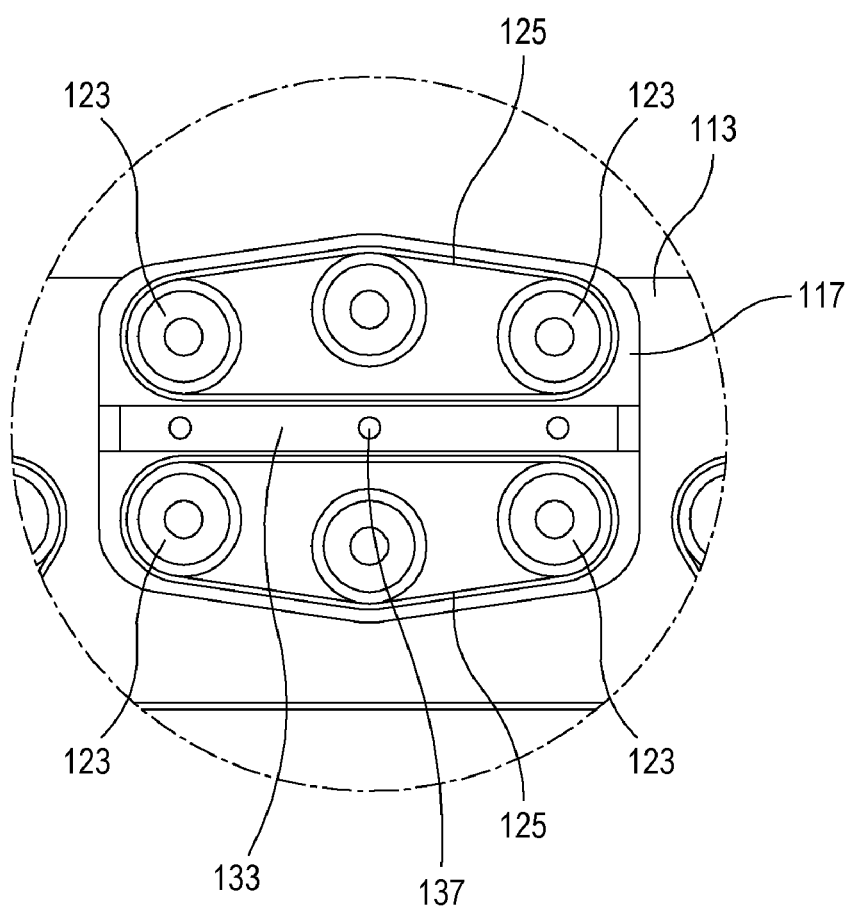

As one embodiment, the transitioning part 110 will be described in more detail with reference to FIGS. 2, 3 and 4. The transitioning part 110 includes a take-in and take-out part for taking in or taking out the item, an item transitioning part for transitioning the item while maintaining the item in the take-in and take-out part, and the fixing part to which the item transitioning part is fixed.

The fixing part includes first and second fixing frames 111 and 113, and functions to support the item transitioning part so that the item can be rotated, by fixing the item transitioning part to be rotatable. The fixing part is fixed to the ground or another frame or the like so that the transitioning part 110 can rotate the item stably.

The item transitioning part includes first and second item transitioning frames 115 and 117, an item transitioning actuator 119 that is disposed on the fixing frame and is driven to transition the first and second item transitioning frames 115 and 117, and an item transitioning shaft 121 that is linked with the item transitioning actuator 119, extends to pass through the first and second fixing frames 111 and 113, and is linked with the first and second item transitioning frames 115 and 117. The item transitioning actuator 119 may employ an electric motor, a rotary cylinder or the like, and may be connected to the item transitioning shaft 121 directly or indirectly through a power transmission device including gears, belts and pulleys or the like. The item transitioning shaft 121 may be connected to the first and second item transitioning frames 115 and 117 through the power transmission device including gears, belts and pulleys or the like. As a result, by employing one item transitioning actuator 119, the first and second item transitioning frames 115 and 117 may be rotated synchronously using the item transitioning shaft 121, and can be driven smoothly at low cost by using one actuator. In some cases, a plurality of item transitioning actuators may be used, by linking item transitioning actuators respectively with each of the first and second item transitioning frames 115 and 117. The first and second item transitioning frames 115 and 117 may be configured to be linked with pulleys fixed to both ends of the item transitioning shaft 121 that is fixed to be rotatable and that passes through the first and second fixing frames 111 and 113. The first and second item transitioning frames 115 and 117 may be linked with each other depending on the actuation of the item transitioning shaft 121. A spline shaft may be employed for the item transitioning shaft 121, and parts of the power transmission device including pulleys or the like may move relatively in an axial direction. It is also possible to freely adjust the width of the transitioning part 110 according to the size of the item.

The take-in and take-out part includes take-in and take-out pulleys 123 that are disposed on inner surfaces of the first and second item transitioning frames 115 and 117, the inner surfaces facing each other, take-in and take-out belts 125 that are linked with the take-in and take-out pulleys 123, and take-in and take-out actuators 127 that are disposed on the first and second fixing frames 111 and 113 and drive the take-in and take-out pulleys 123. The take-in and take-out actuator 127 may be connected to the take-in and take-out pulley 123 directly or indirectly through a power transmission device including gears, belts and pulleys or the like, and may be driven. The take-in and take-out part enables a movement of the item including the take in and the take out of the item within the item transitioning part. The number of take-in and take-out pulleys 123 and the number of the take-in and take-out belts 125 are not limited, and various numbers of the take-in and take-out pulleys 123 and the take-in and take-out belts 125 may be employed within a range that enables the movement of the item. An electric motor, a rotary cylinder or the like may be employed as the take-in and take-out actuator 127, and the take-in and take-out actuator 127 may be disposed on the first and second fixing frames 111 and 113 and may be driven in the same manner.

The fixing part may further include an auxiliary transfer part that assists in taking in or taking out an item into or from the take-in and take-out part, and the auxiliary transfer part is located between the take-in and take-out part of the transitioning part 110 and the transferring part 140. By having the auxiliary transfer part, items with various sizes can be smoothly taken in or taken out into or from the take-in and take-out part, and it is possible to take in and take out the item smoothly even when the length of the item in the transfer direction is different by transitioning the direction of one item through rotation. The auxiliary transfer part includes auxiliary transfer pulleys 129 that are disposed on inner surfaces of the first and second fixing frames 111 and 113, the inner surfaces facing each other, and auxiliary transfer belts 131 that are linked with the auxiliary transfer pulleys 129. The auxiliary transfer pulley 129 is linked with the take-in and take-out actuator 127. A rotary shaft of the auxiliary transfer pulley 129 may be linked with a power transmission device which is connected directly or connected through gears, pulleys and belts and the like, and may be operated in accordance with the driving of the take-in and take-out actuator 127. The number of auxiliary transfer pulleys 129 and the number of auxiliary transfer belts 131 are not limited, but various numbers of the auxiliary transfer pulleys 129 and the auxiliary transfer belts 131 may be employed within a range that enables the movement of the item.

An item fixing part according to one embodiment will be described in detail with reference to FIGS. 3 and 4. The item fixing part may be further included in at least one of the first or second item transitioning frames 115 or 117. The item fixing part functions to fix the item so that the item can be transitioned while stably maintaining the item in the item transitioning part. The item fixing part is disposed at a fixing position (for example, a first position for inspecting the item) where the item is to be fixed, and presses and fixes the item in a direction perpendicular to the item transfer direction at a position where the item is being transitioned. In this embodiment, the case where the second item transitioning frame 117 includes the item fixing part will be described. The item fixing part includes an item fixing shaft 134, an item fixing actuator 135 and a fixing end 133 that are connected to each other, and when the item fixing actuator 135 moves the item fixing shaft 134, the fixing end 133 connected to the other end thereof is also moved to press and fix the item. The item fixing actuator 135 is fixed to the second item transitioning frame 117 and may be implemented by employing an actuator such as a motor, cylinder or the like that is capable of performing a linear motion. It is desirable that the fixing end 133 is made of a material having a lower strength than the item to prevent breakage of the item. In addition, the item fixing part may further include a sensing part 137 for detecting whether the item is located at the fixing position. The sensing part 137 may be implemented by employing means that can detect the presence or absence of an item, such as an optical sensor or the like, including an infrared sensor. The item may be fixed after confirming by the sensing part 137 that the item is located at the fixing position.

Figure 5:
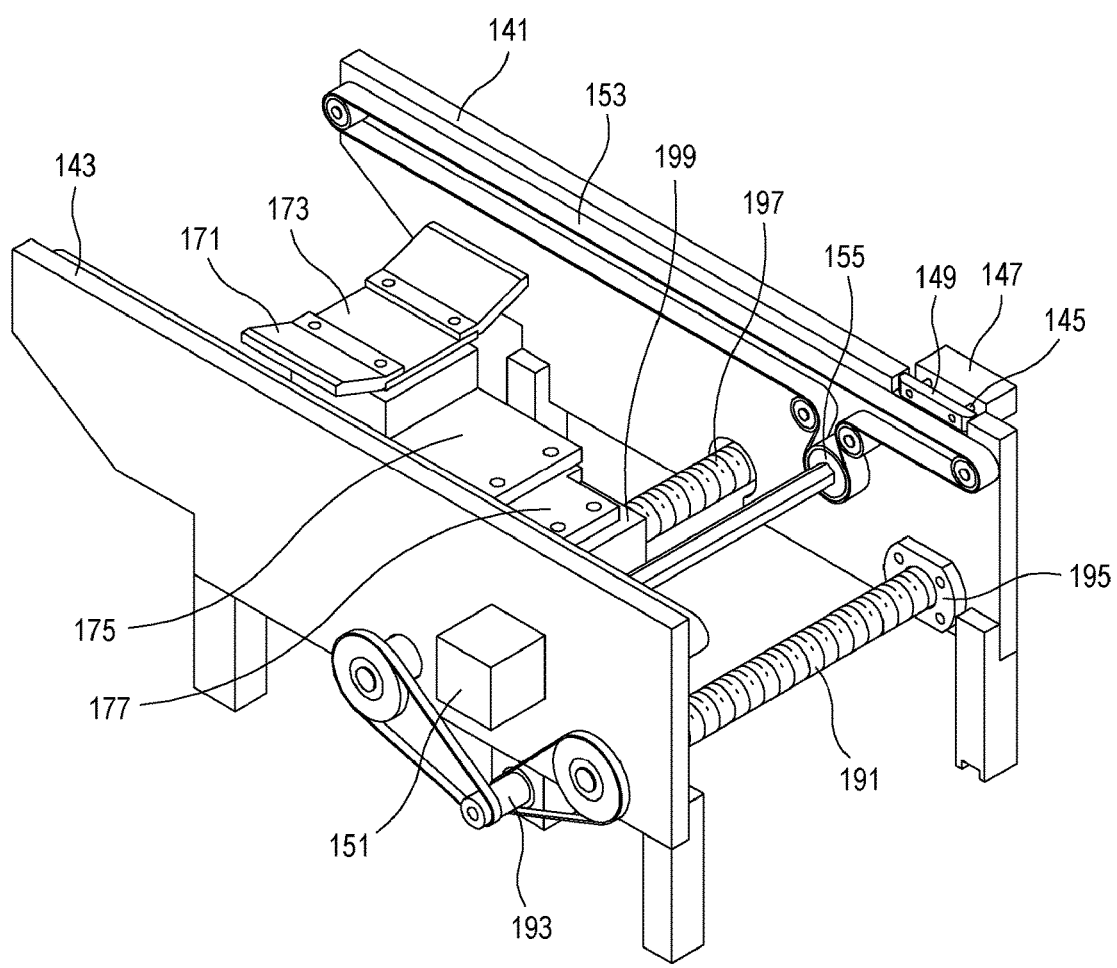
FIGS. 5 and 6 are perspective views of a transferring part and rotating part according to the present disclosure.
Figure 6:
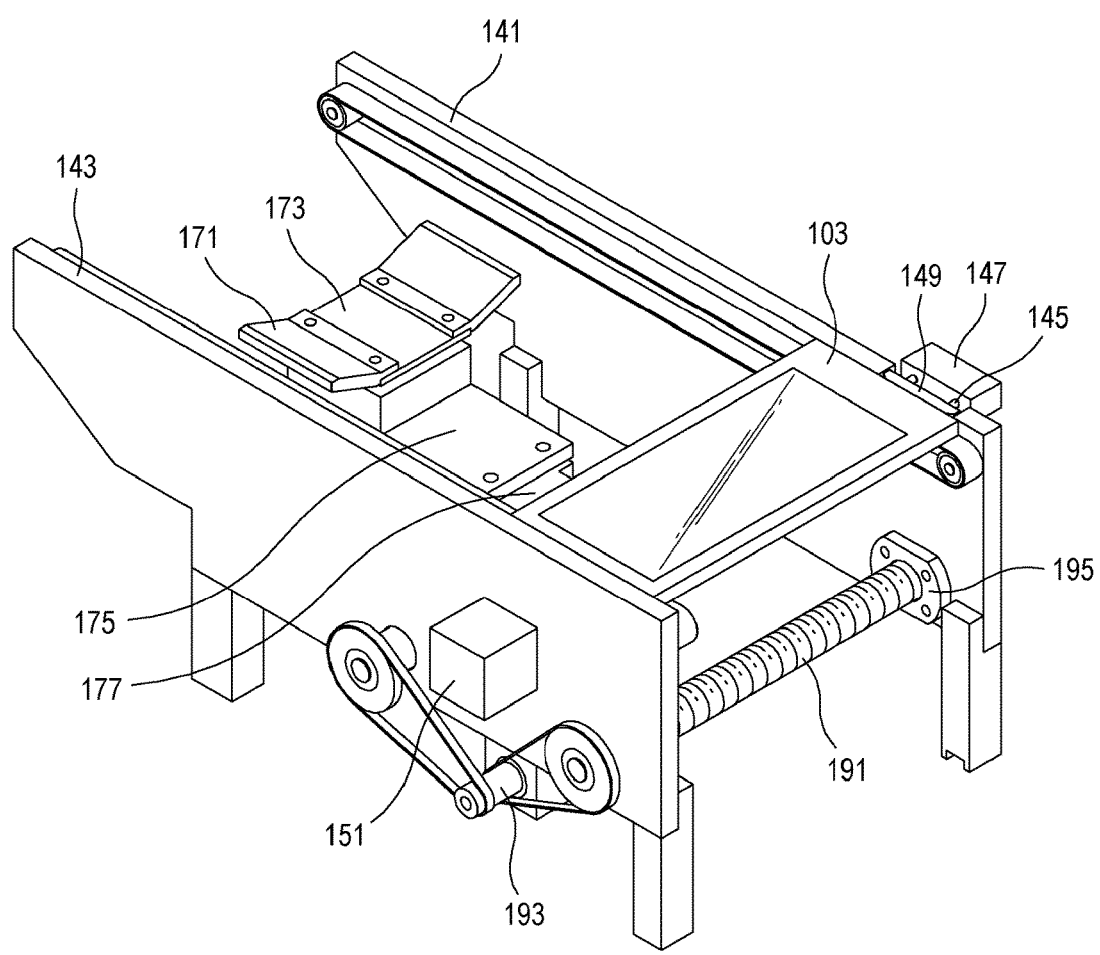
Figure 7:
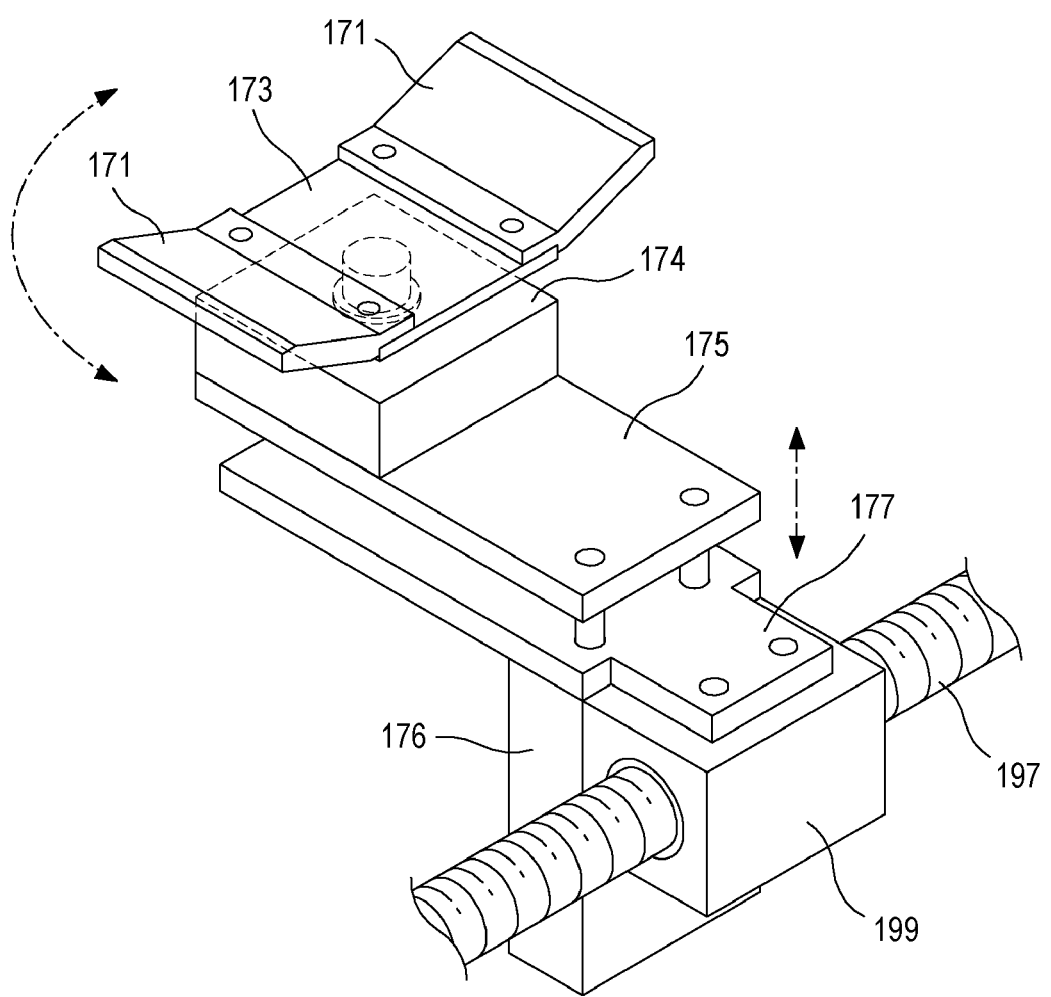
FIG. 7 is a perspective view of a rotating part according to the present disclosure.

The rotating part 170 according to one embodiment will be described in more detail with reference to FIGS. 5 to 7. The rotating part 170 includes a supporting part for supporting the bottom surface of the item located at the transferring part 140, a rotation actuation part for rotating the supporting part, and a raising-and-lowering part for raising and lowering the item.

The supporting part according to the present embodiment includes a first rotation frame 173 and a support 171 which is provided to protrude upward from the first rotation frame 173. It is desirable that the support 171 stably supports the item while maintaining a balance of the item. Regardless of the number and material of the support 171, the support may be separately manufactured and combined, or formed together with the first rotation frame 173. The support 171 may further include a contact end that has a lower strength than the item and provides a high frictional force so that the item can be stably rotated by increasing the frictional force with the item, and protecting the item at the position in contact with the item. For example, the contact end may be made of a material such as rubber, resin or the like.

The first rotation frame 173 may rotate in conjunction with a rotation actuator 174 fixed to the second rotation frame 175. For example, a main body of the rotation actuator 174 is fixed to the second rotation frame 175, and a rotary shaft of the rotation actuator 174 is fixed to the first rotation frame 173, so that, when a driving force is supplied from the rotation actuator 174, the first rotation frame 173 rotates. Thus, the item supported on top of the first rotation frame 173 may rotate together with the first rotation frame 173. An electric motor, a rotary cylinder or the like may be employed and implemented as the rotation actuator 174.

The second rotation frame 175 may be raised and lowered in conjunction with a raising-and-lowering actuator 176 fixed to a third rotation frame 177. For example, one end of the raising-and-lowering actuator 176 is fixed to the third rotation frame 177, and the other end of the raising-and-lowering actuator 176 is fixed to the second rotation frame 175, so that, when a driving force is supplied from the raising-and-lowering actuator 176, the second rotation frame 175 is raised or lowered. Thus, both the second rotation frame 175 and the first rotation frame 173 may be raised or lowered, and the item supported on the first rotation frame 173 may be also raised and lowered. It is desirable that the third rotation frame 177 is fixed to the ground or other parts and disposed at a position where the support 171 can support the bottom surface of the item.

The transferring part 140 according to one embodiment will be described in more detail with reference to FIGS. 5 and 6. The transferring part 140 includes transfer frames 141 and 143, transfer pulleys 155 that are disposed on the transfer frames 141 and 143, transfer belts 153 that are linked with the transfer pulleys 155, and a transfer actuator 151 that provides a driving force to the transfer pulleys 155. The item is placed on the transfer belt 153 and transferred in accordance with the movement of the transfer belt 153. An electric motor, a rotary cylinder or the like may be employed and implemented as the transfer actuator 151, and the transfer pulley 155 and the transfer belt 153 may employ various types of pulleys and belts including a timing pulley and a timing belt. The transferring part 140 may further include a transfer shaft that passes through the transfer frames 141 and 143 so that one transfer actuator 151 is linked with a plurality of transfer pulleys 155. For example, the transfer shaft may be a spline shaft.

A rotation direction of the transfer pulley 155 may be reversed in accordance with a actuation direction of the transfer actuator 151, and a transfer direction of the transfer belt 153 linked with the transfer pulley 155 may also be reversed. The transfer frames 141 and 143 include first and second transfer frames 141 and 143 arranged in parallel, and the first transfer frame 141 includes a position adjustment part for placing the item at a first position. The position adjustment part includes a position adjustment shaft 145, a position adjustment actuator 147 that is fixed to the first transfer frame 141 and is connected to one end of the position adjustment shaft 145 to advance and retreat the position adjustment shaft 145, and a position adjustment end 149 that is connected to the other end of the position adjustment shaft 145. With reference to FIG. 6, when an item 103 is sensed to be located approximately at the first position, the transfer actuator 151 is stopped and the position adjustment actuator 147 operates to align the item 103 at the first position, so that the position adjustment end 149 can press the item 103 and align the item 103 at the first position. The position adjustment actuator 147 may be implemented by employing various actuators such as a motor, a cylinder or the like which are capable of performing a linear motion. It is desirable that the position adjustment end 149 is made of a material having a lower strength than the item 103 to prevent breakage of the item.

A width adjusting part according to one embodiment will be described in detail with reference to FIG. 5. The item transfer apparatus 100 according to the present disclosure may further include the width adjusting part that adjusts a width of the item transfer apparatus 100. By including the width adjusting part, it is possible to transfer items with various sizes using one item transfer apparatus 100.

The width adjusting part includes a first screw 191 that passes through the first and second transfer frames 141 and 143, a width adjusting actuator 193 that is installed in any one of the first or second transfer frames 141 or 143 and linked with one end of the first screw 191, and a first nut 195 that is fixed to the transfer frame located at the other end of the first screw 191 and fastened to the first screw 191. The width adjusting actuator 193 may be implemented by employing an electric motor, a rotary cylinder or the like. The width adjusting actuator 193 can rotate the first screw 191 by generating a rotational driving force. The rotating of the first screw 191 can move the transfer frame fastened to the first nut 195 in the axial direction, and the width between the first and second transfer frames 141 and 143 can be adjusted mutually.

The item transfer apparatus 100 according to the present embodiment may further include a second screw 197 that passes through the first and second transfer frames 141 and 143, and the second screw 197 may be fastened to a second nut 199 provided in the third rotation frame 177. The second screw 197 is linked with the width adjusting actuator 193, and the first and second screws 191 and 197 may be driven at the same rotational speed. The linking of the first and second screws 191 and 197 may be implemented by employing various power transmission means for transmitting a rotational driving force such as gears or pulleys and belts. Here, pitches of the first and second screws 191 and 197 are adjusted differently so that axial movement distances of the first nut 195 and the second nut 199 with respect to the same rotation of the width adjusting actuator 193 can be adjusted differently. In particular, the pitch of the first screw 191 can be adjusted to be twice as large as the pitch of the second screw 197, and an axial movement distance of the first nut 195 becomes twice that of the second nut 199 for the same rotation of the first and second screws 191 and 197. That is, since the first nut 195 is fixed to the first or second transfer frame 141 or 143, the third rotation frame 177 to which the second nut 199 is fixed moves only half of the width adjustment distance. When the rotating part 170 is initially located at a center of the first and second transfer frames 141 and 143, the rotating part 170 can always be maintained at the center of the first and second transfer frames 141 and 143 regardless of the width adjustment of the first and second transfer frames 141 and 143. In addition, the width adjustment of the transferring part 140 can be linked with the transitioning part 110 by fixing the transferring part 140 to the transitioning part 110. Specifically, by connecting the first transfer frame 141 to the first fixing frame 111 and by connecting the second transfer frame 143 to the second fixing frame 113, a movement in the width direction between the first and second transfer frames 141 and 143 can be transferred to the first and second fixing frames 111 and 113.

Figure 8:
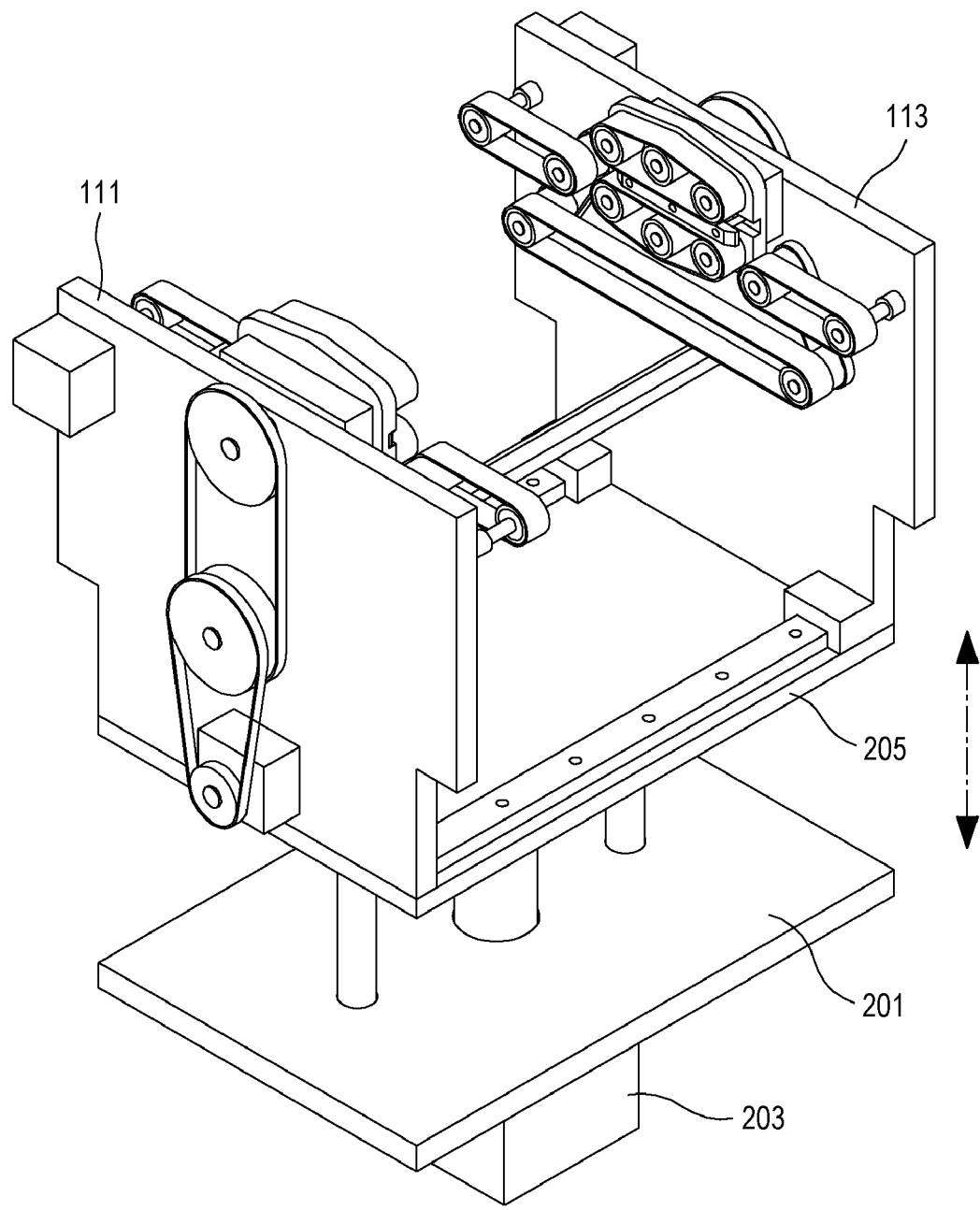
FIG. 8 is a perspective view of a transitioning part according to the present disclosure including a height adjustment part.
Figure 9:
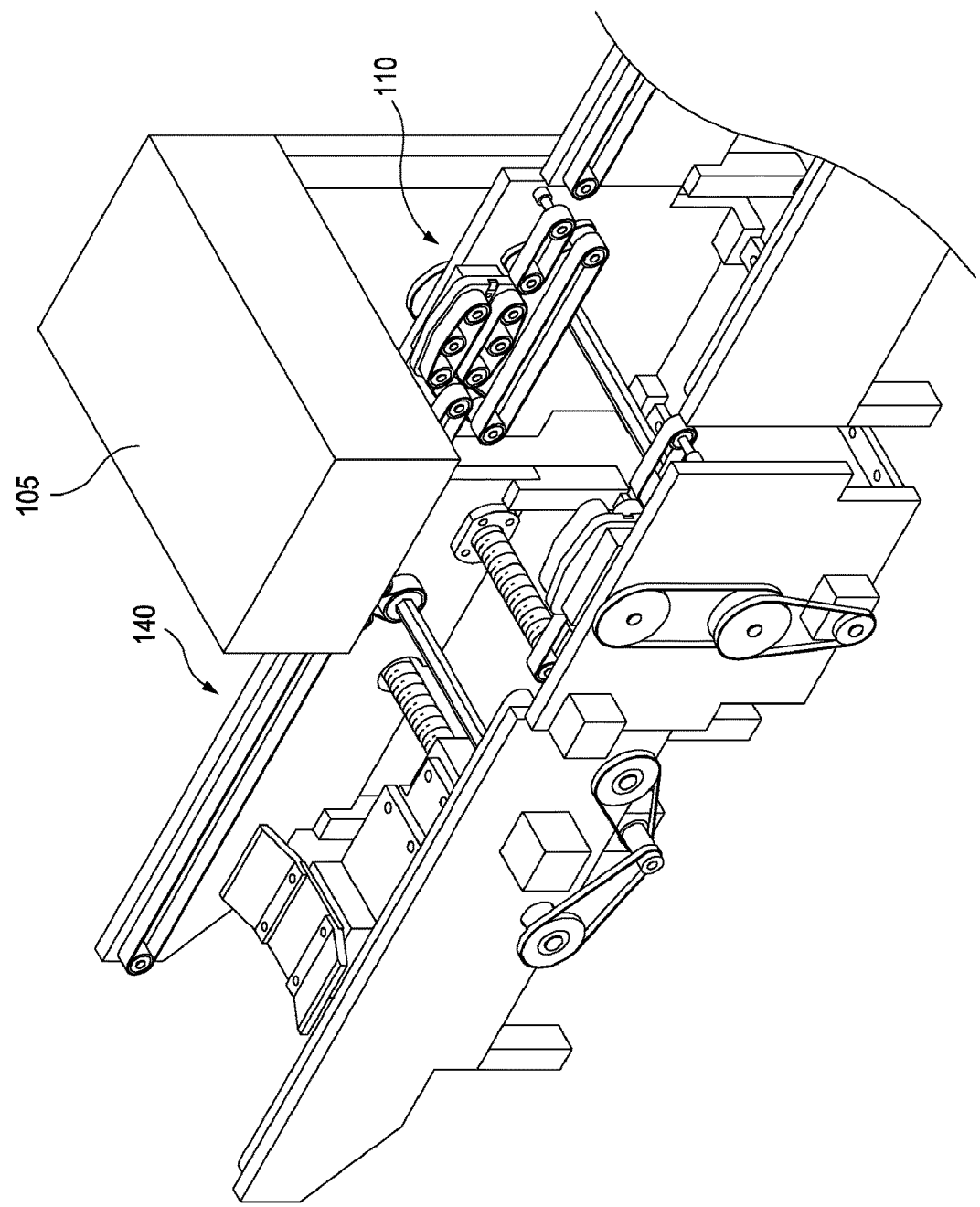
FIG. 9 is a perspective view of an item inspection apparatus according to the present disclosure.

An item inspection apparatus including the item transfer apparatus 100 will be described in more detail with reference to FIGS. 8 and 9. The item inspection apparatus according to the present disclosure includes an inspecting part 105 for inspecting an item in the item transfer apparatus 100 described above. In the present embodiment, the item includes various items which need to be inspected, for example, a mobile phone case may be considered as an item. The inspecting part 105 may be located at various places, but in the present embodiment, a case in which the inspecting part 105 is located above the item transfer apparatus 100 will be described. The inspecting part 105 may include one or more inspection apparatuses capable of inspecting a form of the item, such as a surface, a height, a shape and the like, and may include two-dimensional or three-dimensional inspection apparatuses. The inspecting part 105 may further include an irradiation part that irradiates a pattern light, a measurement part including a photographing portion for photographing the item, and a controller that generates a three-dimensional image of the item and compares the generated three-dimensional image with reference data.

The item inspection apparatus may further include a height adjustment part for adjusting the height of the inspecting part 105 or the transitioning part 110 because a distance between the inspecting part 105 and the item to be inspected needs to be kept constant. In the present embodiment, the height adjustment part is connected to the transitioning part 110, and the height adjustment part may include a support frame 201 and a height adjustment actuator 203 that is fixed to the support frame 201 to adjust the height of the fixing part. The height adjustment actuator 203 may adjust the height of the first and second fixing frames 111 and 113 directly or using a power transmission device including pulleys, belts, screws or nuts or the like. The height adjustment actuator 203 may be implemented by including various types of actuators including an electric motor or a hydraulic cylinder. In the present embodiment, the first and second fixing frames 111 and 113 are supported by a third fixing frame 205, and the height of the third fixing frame 205 is adjusted by driving the height adjustment actuator 203.

An item transfer method according to the present disclosure will be described with reference to FIGS. 10 to 17. The item transfer method according to the present disclosure includes transferring an item from an initial position; transitioning to front and rear surfaces and top and bottom surfaces with respect to a transfer direction of the item; returning the item in an opposite direction to the transfer direction in the state where the top and bottom surfaces of the item are transitioned; rotating the item while maintaining the top and bottom surfaces of the item; and repeating the act of transferring the item from the initial position and the act of transitioning to the front and rear surfaces and the top and bottom surfaces with respect to the transfer direction of the item. In addition, the item transfer method according to the present disclosure may further include discharging the item in the transfer direction of the item.

Figure 10:
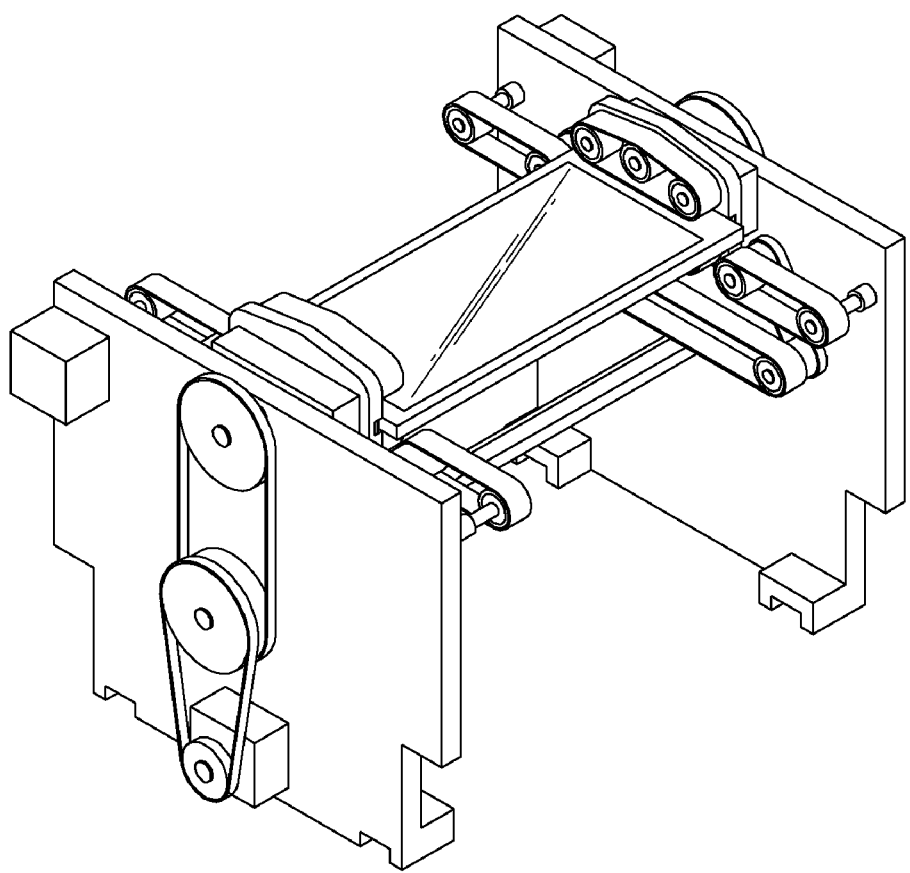
FIGS. 10 to 13 are explanatory views showing transitioning operation according to the present disclosure.
Figure 11:
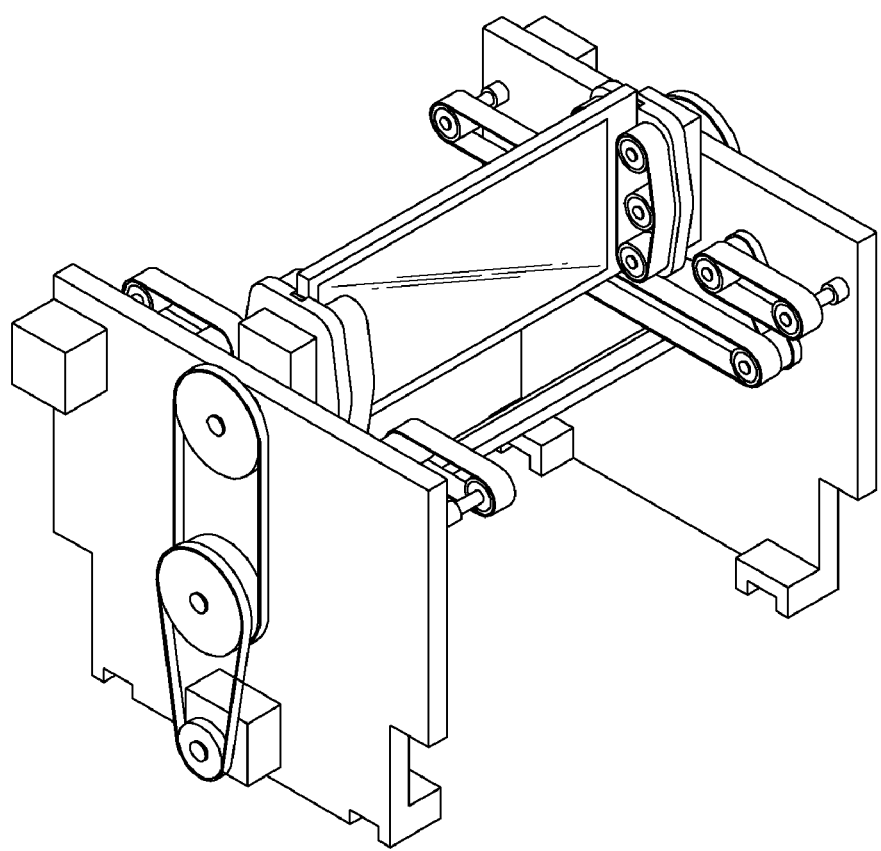
Figure 12:
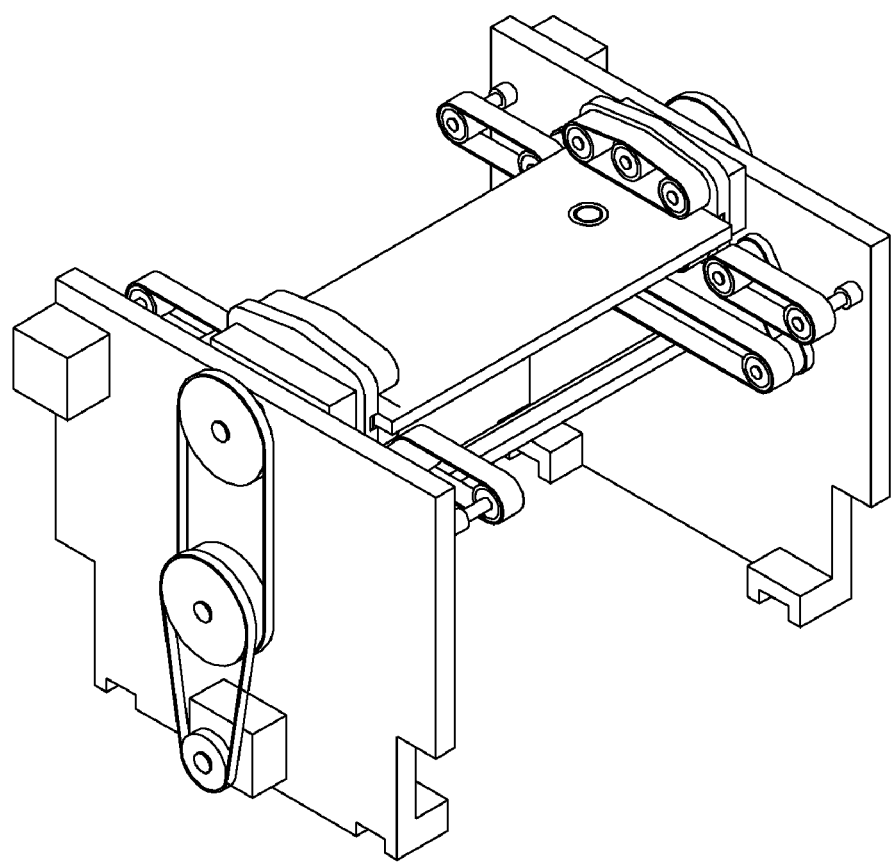
Figure 13:
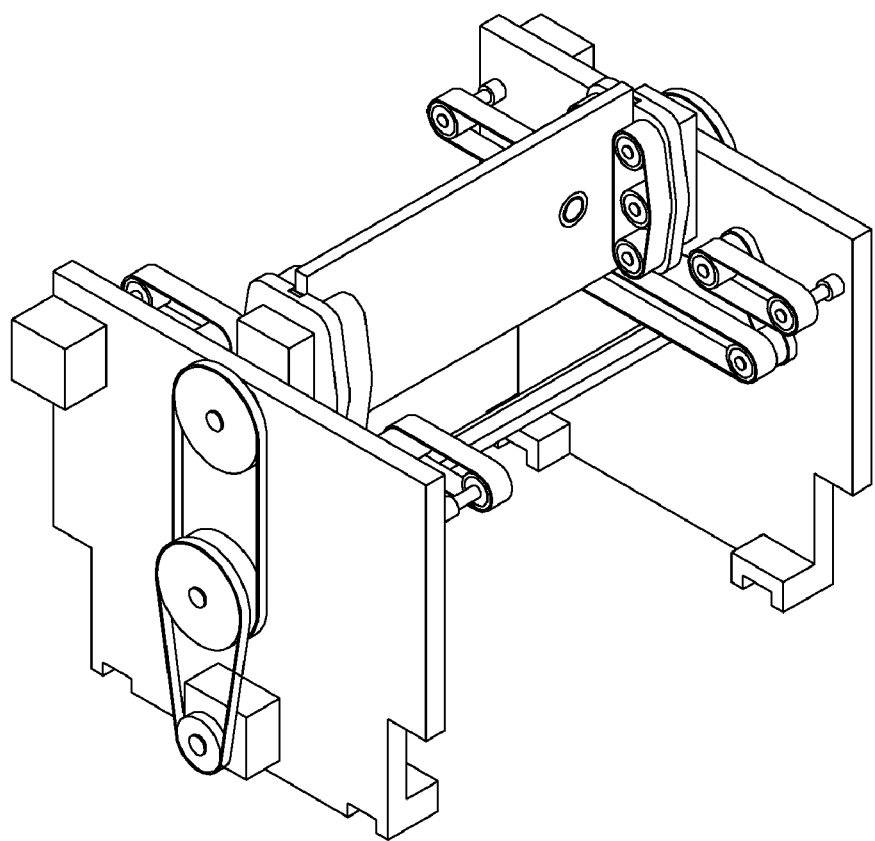
Figure 14:
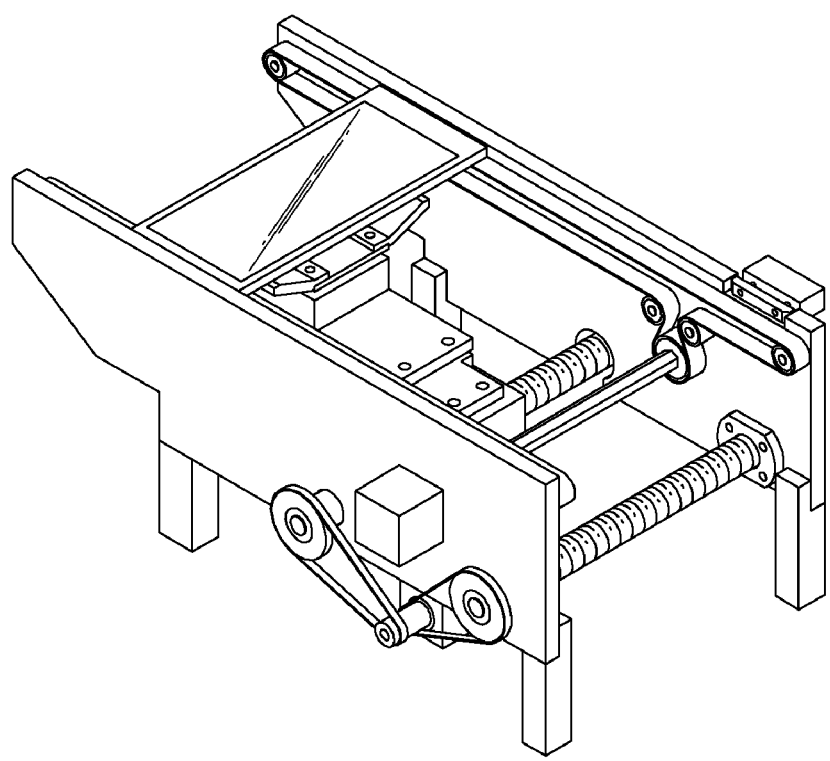
FIGS. 14 to 17 are explanatory views showing rotation operation according to the present disclosure.
Figure 15:
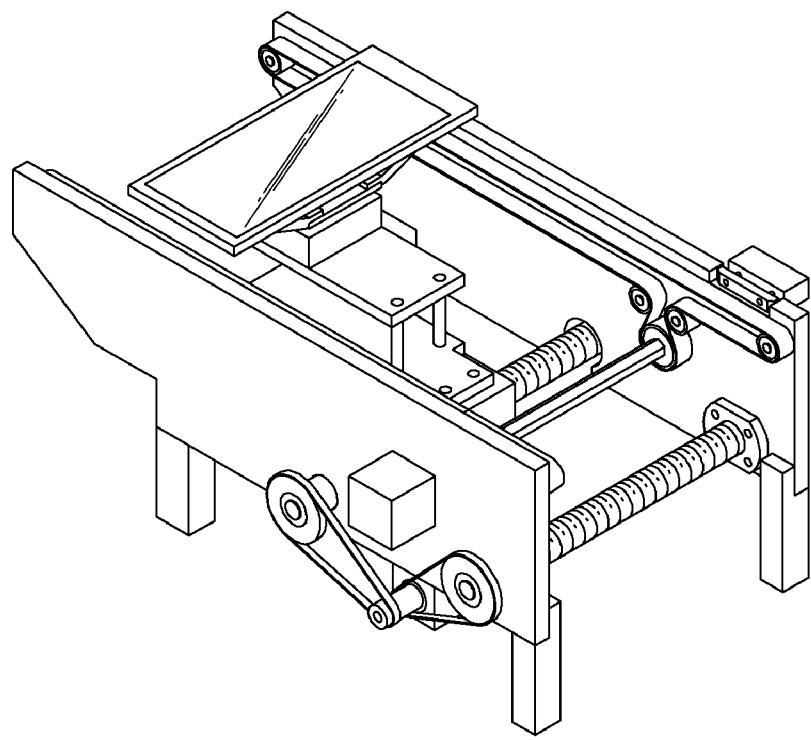
Figure 16:
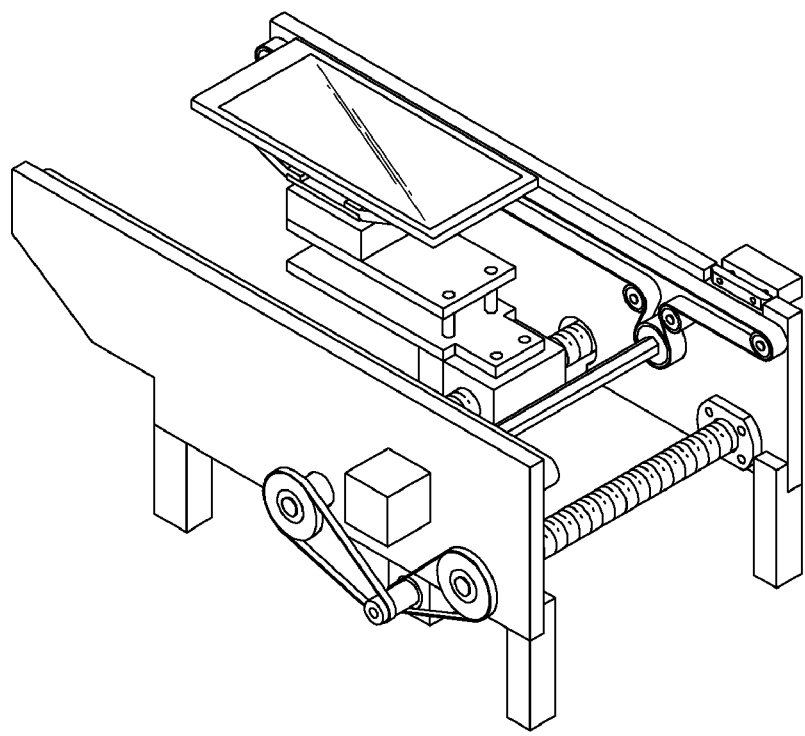
Figure 17:
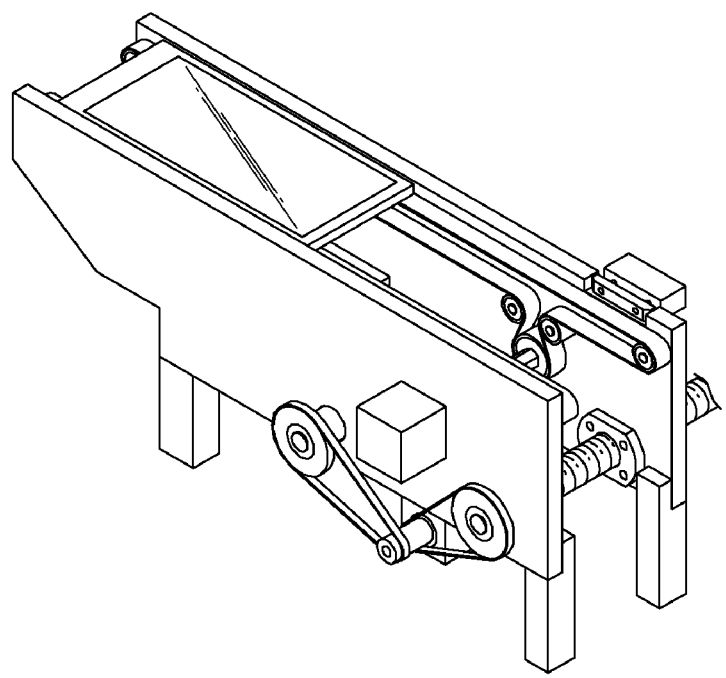

FIGS. 10 and 13 illustrate the transitioning to the front and rear surfaces and the top and bottom surfaces with respect to the transfer direction of the item in more detail. The transitioning the item may transition the transferred item, fix the item, and then provide the front and rear surfaces or top and bottom surfaces of the item. FIGS. 10 to 13 illustrate the transitioning process of the item which provides the front and rear surfaces and the top and bottom surfaces of each item. Thus, a particular surface of the item may be provided at the upper part, or the front and rear surfaces or the top and bottom surfaces of the item can be transitioned.

FIGS. 14 to 17 illustrate in detail the rotating of the item while maintaining the top and bottom surfaces of the item. The rotating of the item while maintaining the top and bottom surfaces of the item may include rotating the returned item while maintaining the top and bottom surfaces of the item, that are located at the top and bottom of the item, and raising and lowering the item. The rotating of the item while maintaining the top and bottom surfaces of the item, which includes the raising and lowering of the item, includes raising the item when the item is located at a predetermined position, rotating the item by a predetermined angle, and lowering the item again. In case the raising and lowering of the item is included, there is the advantage that the item can be smoothly rotated even when a rotation space of the item in the item transfer apparatus cannot be secured in the rotating of the item. When the item is rotated, the left and right surfaces and the front and rear surfaces of the item may be changed by rotating the item by 90 degrees. By changing the left and right surfaces and the front and rear surfaces of the item, the transitioning the item and the repeating of the act of transferring the item and the act of transitioning the item may each provide surfaces which are different from each other. By including the above-described operations, there is the effect that six different surfaces may be provided through one item transfer method.

An item inspection method will be described in more detail using the above-described item transfer method. The item inspection method according to the present disclosure generally uses the item transfer method that can transfer the item to provide six surfaces of the item, and it is possible to efficiently inspect each surface of the item in one sequence by employing an inspection apparatus (for example, the inspecting part 105).

The item inspection method includes transferring the item from an initial position to a first position; inspecting the top surface of the item at the first position; inspecting the item by transitioning the front and rear surfaces of the item to face upwards; transitioning the bottom surface of the item to face upwards; returning the item to the initial position; rotating the item by 90 degrees at the initial position while maintaining the top and bottom surfaces of the item; transferring the item again to the first position; inspecting the bottom surface of the item at the first position; and inspecting the item by transitioning the left and right surfaces of the item to face upwards. In addition, the item inspection method may further include discharging the item along a transfer direction of the item.

Since the six surfaces of the item face at least once upwards through the item inspection method of the present disclosure, the six surfaces of the item may be inspected while minimizing the number of inspection apparatuses located above the item. This has the advantage that all surfaces of the item can be inspected in a time-efficient and low-cost manner. However, it is not limited to six surfaces of an item, but methods that inspect item surfaces exceeding six surfaces or having less than six surfaces are possible, depending on the transitioning and rotation angle.

What is claimed is:

1. An item transfer apparatus for transferring an item, comprising:
    a transitioning part configured to transition the item such that at least one of front, rear, top and bottom surfaces of the item faces upwards when viewed in a transfer direction of the item;
    a transferring part configured to transfer the item to the transitioning part; and
        a rotating part configured to rotate the item such that front, rear, left and right surfaces of the item are changed, without changing top and bottom surfaces of the item when viewed in the transfer direction,
    wherein the transferring part is configured to:
        transfer the item, which has been transitioned by the transitioning part to the rotating part; and
    transfer the item, which has been rotated by the rotating part back to the transitioning part.

2. The item transfer apparatus of claim 1, wherein the transitioning part includes:
    a take-in and take-out part configured to take in or take out the item;
    an item transitioning part configured to transition the item while maintaining the item in the take-in and take-out part; and
    a fixing part to which the item transitioning part is fixed.

3. The item transfer apparatus of claim 2,
    wherein the fixing part includes first and second fixing frames,
    wherein the item transitioning part includes:
        first and second item transitioning frames that are disposed on inner surfaces of the first and second fixing frames, the inner surfaces facing each other;
        an item transitioning actuator that is disposed on the first fixing frame and driven to transition the first and second item transitioning frames; and
        an item transitioning shaft that is linked with the item transitioning actuator, extended to pass through the first and second fixing frames, and linked with the first and second item transitioning frames, and
    wherein the take-in and take-out part includes:
        take-in and take-out pulleys that are disposed on inner surfaces of the first and second item transitioning frames, the inner surfaces facing each other;
        take-in and take-out belts that are linked with the take-in and take-out pulleys; and
        take-in and take-out actuators that are disposed on the first and second fixing frames and configured to drive the take-in and take-out pulleys.

4. The item transfer apparatus of claim 3,
    wherein the fixing part further includes an auxiliary transfer part that is located between the transferring part and the take-in and take-out part,
    wherein the auxiliary transfer part includes auxiliary transfer pulleys that are disposed on the first and second fixing frames and auxiliary transfer belts that are linked with the auxiliary transfer pulleys, and
    wherein the auxiliary transfer pulleys are driven by the take-in and take-out actuators.

5. The item transfer apparatus of claim 3,
    wherein the transitioning part further includes an item fixing part that is disposed on at least one of the first and second item transitioning frames, and
    wherein the item fixing part includes an item fixing shaft, an item fixing actuator that is connected to one end of the item fixing shaft and a fixing end that is connected to the item fixing shaft.

6. The item transfer apparatus of claim 5, wherein the item fixing part further includes a sensing part configured to detect whether the item is present or absent.

7. The item transfer apparatus of claim 3, wherein the rotating part includes:
    a supporting part configured to support a bottom surface of the item located at the transferring part;
    a rotation actuation part configured to rotate the supporting part; and
    a raising-and-lowering part configured to raise and lower the item.

8. The item transfer apparatus of claim 7,
    wherein the supporting part includes a first rotation frame and a support that protrudes upwards from the first rotation frame,
    wherein the rotation actuation part includes a second rotation frame and a rotation actuator that is fixed to the second rotation frame and configured to rotate the first rotation frame, and
    wherein the raising-and-lowering part includes a third rotation frame and a raising-and-lowering actuator that is fixed to the third rotation frame and configured to raise and lower the second rotation frame.

9. The item transfer apparatus of claim 8, wherein the transferring part includes:
    a transfer frame;
    a transfer pulley that is disposed on the transfer frame;
    a transfer belt that is linked with the transfer pulley; and
    a transfer actuator configured to provide a driving force to the transfer pulley.

10. The item transfer apparatus of claim 9,
wherein the transfer frame includes first and second transfer frames arranged in parallel, and
wherein the first transfer frame includes a position adjustment part configured to place the item at a first position.

11. The item transfer apparatus of claim 10, wherein the position adjustment part includes:
a position adjustment shaft;
a position adjustment actuator that is fixed to the first transfer frame and configured to advance and retreat the position adjustment shaft; and
a position adjustment end that is connected to the position adjustment shaft.

12. The item transfer apparatus of claim 11, further comprising:
a width adjusting part.

13. The item transfer apparatus of claim 12,
wherein the first transfer frame is connected to the first fixing frame, and
wherein the second transfer frame is connected to the second fixing frame.

14. An item inspection apparatus comprising:
a transitioning part configured to transition the item such that at least one of front, rear, top and bottom surfaces of the item faces upwards when viewed in a transfer direction of the item;
a transferring part configured to transfer the item to the transitioning part;
a rotating part configured to rotate the item such that front, rear, left and right surfaces of the item are changed, without changing top and bottom surfaces of the item when viewed in the transfer direction; and
an inspecting part configured to inspect a shape of the item,
wherein the transferring part is configured to:
transfer the item, which has been transitioned by the transitioning part to the rotating part; and
transfer the item, which has been rotated by the rotating part back to the transitioning part,
wherein the transitioning part includes:
a take-in and take-out part configured to take in or take out the item;
an item transitioning part configured to transition the item while maintaining the item in the take-in and take-out part; and
a fixing part to which the item transitioning part is fixed.

15. The item inspection apparatus of claim 14, further comprising:
a height adjustment part configured to adjust a height of the transitioning part or the inspecting part.

16. The item inspection apparatus of claim 15, wherein the height adjustment part includes:
a support frame; and
a height adjustment actuator that is fixed to the support frame and configured to adjust a height of the fixing part.

17. An item transfer method comprising:
transferring an item from an initial position;
transitioning the item such that at least one of front, rear, top and bottom surfaces of the item faces upwards when viewed in a transfer direction of the item;
returning the item to the initial position in a state where top and bottom surfaces of the item are transitioned;
rotating the item such that front, rear, left and right surfaces of the item are changed, without changing top and bottom surfaces of the item when viewed in the transfer direction; and
repeating the act of transferring the item from the initial position, the act of transitioning the item, the act of returning the item to the initial position, and the act of rotating the item.

18. The item transfer method of claim 17, further comprising:
discharging the item in the transfer direction of the item, after the act of repeating the act of transferring the item from the initial position, the act of transitioning the item, the act of returning the item to the initial position, and the act of rotating the item.

19. The item transfer method of claim 17, wherein the act of rotating the item such that front, rear, left and right surfaces of the item are changed, without changing top and bottom surfaces of the item when viewed in the transfer direction includes:
raising and lowering the item.

20. The item transfer method of claim 19, wherein the act of rotating the item such that front, rear, left and right surfaces of the item are changed, without changing top and bottom surfaces of the item when viewed in the transfer direction includes:
rotating the item by 90 degrees.

* * * * *